US009883811B2

United States Patent
Kang et al.

(10) Patent No.: US 9,883,811 B2
(45) Date of Patent: Feb. 6, 2018

(54) APPARATUS AND METHOD FOR DETECTING BIOMETRIC INFORMATION

(71) Applicant: SAMSUNG ELECTRONICS CO., LTD., Suwon-si (KR)

(72) Inventors: Jaemin Kang, Seoul (KR); Yongjoo Kwon, Yongin-si (KR); Sunkwon Kim, Suwon-si (KR); Younho Kim, Hwaseong-si (KR); Sangyun Park, Hwaseong-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 242 days.

(21) Appl. No.: 14/702,223

(22) Filed: May 1, 2015

(65) Prior Publication Data

US 2016/0106325 A1    Apr. 21, 2016

(30) Foreign Application Priority Data

Oct. 15, 2014  (KR) .................. 10-2014-0139069

(51) Int. Cl.
| | | |
|---|---|---|
| *A61B 5/00* | (2006.01) | |
| *A61B 5/026* | (2006.01) | |
| *A61B 5/021* | (2006.01) | |

(52) U.S. Cl.
CPC ........ *A61B 5/0261* (2013.01); *A61B 5/02125* (2013.01); *A61B 5/489* (2013.01); *A61B 5/6802* (2013.01); *A61B 5/6824* (2013.01)

(58) Field of Classification Search
CPC ... A61B 5/0261; A61B 5/02125; A61B 5/489; A61B 5/6802; A61B 5/6824
See application file for complete search history.

(56) References Cited

U.S. PATENT DOCUMENTS

| | | | |
|---|---|---|---|
| 7,364,549 B2 | 4/2008 | Hashimoto et al. | |
| 2010/0185068 A1* | 7/2010 | Park ...................... | A61B 5/021 600/324 |
| 2015/0374245 A1* | 12/2015 | Szilagyi ............. | A61B 5/14551 600/479 |
| 2016/0081563 A1* | 3/2016 | Wiard .................. | A61B 5/0285 600/485 |

FOREIGN PATENT DOCUMENTS

| | | | |
|---|---|---|---|
| JP | 7-299043 A | 11/1995 | |
| JP | 4229919 B2 | 2/2009 | |
| KR | 1020080009030 A | 1/2008 | |
| KR | 10-1007355 B1 | 1/2011 | |
| KR | 10-1038425 B1 | 6/2011 | |

* cited by examiner

*Primary Examiner* — Scott Getzow

(74) *Attorney, Agent, or Firm* — Sughrue Mion, PLLC

(57) ABSTRACT

Provided is an apparatus and method for detecting biometric information. The apparatus may include a biometric signal measurer comprising a light-receiving element and a plurality of light-emitting elements; and a processor including a tracking unit configured to sequentially drive the plurality of light-emitting elements, receive a signal detected by the light-receiving element, and determine a tracking line that connects at least two positions of a radial artery of the object from the received signal; and an analyzing unit configured to detect a pulse wave signal at the at least two points on the tracking line and analyze biometric information from the detected pulse wave signal.

12 Claims, 18 Drawing Sheets

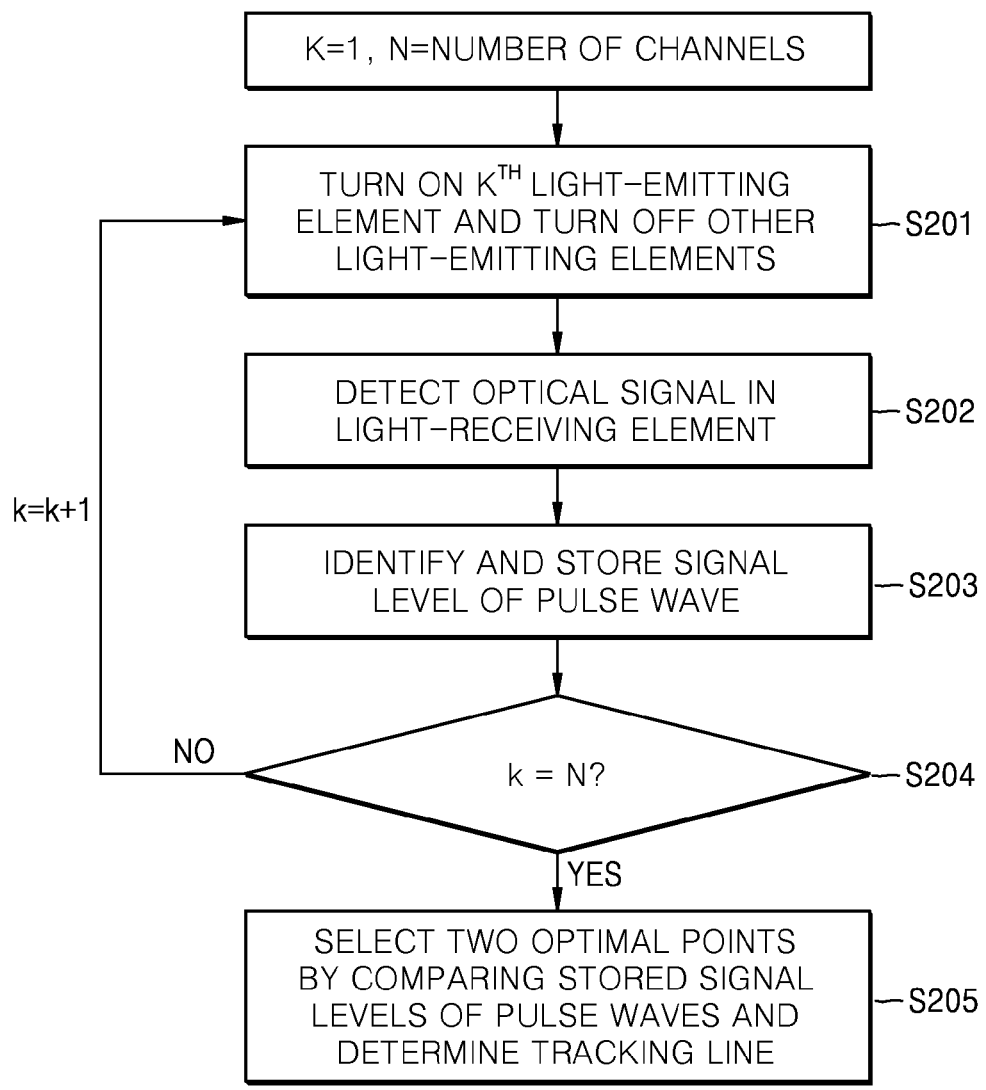

APPARATUS AND METHOD FOR DETECTING BIOMETRIC INFORMATION

CROSS-REFERENCE TO RELATED APPLICATION

This application claims priority from Korean Patent Application No. 10-2014-0139069, filed on Oct. 15, 2014 in the Korean Intellectual Property Office, the disclosure of which is incorporated herein in its entirety by reference.

BACKGROUND

1. Field

Apparatuses and methods consistent with exemplary embodiments relate to detecting biometric information.

2. Description of the Related Art

With the increasing interest in health, various types of biometric information detection apparatuses have been developed. In particular, with the spread of a variety of wearable devices, wearable devices specialized for health care have been developed.

Methods of detecting biometric information such as pulse waves may be roughly divided into invasive methods and noninvasive methods, among which the noninvasive methods are widely used because of simply detecting pulse waves without causing pain to a subject.

For accurate pulse wave analysis (PWA), information based on an optical signal or a pressure signal on a specific body surface of a subject needs to be obtained. Based on such information, biometric information of the subject may be obtained, and to reduce measuring errors, various methods are used.

SUMMARY

One or more exemplary embodiments provide an apparatus and method for detecting biometric information.

According to an aspect of an exemplary embodiment, there is provided an apparatus for detecting biometric information of an object including: a biometric signal measurer including a light-receiving element and a plurality of light-emitting elements; and a processor comprising a tracking unit configured to sequentially drive the plurality of light-emitting elements, receive a signal detected by the light-receiving element, and determine a tracking line that connects at least two positions of a radial artery of the object from the received signal, and an analyzing unit configured to detect a pulse wave signal at the at least two points on the tracking line and analyze biometric information from the detected pulse wave signal.

The plurality of light-emitting elements are arranged to surround the light-receiving elements.

The plurality of light-emitting elements are arranged isotropically with respect to the light-receiving element.

The biometric signal measurer may further include a plurality of light-receiving elements including the light-receiving element, the plurality of light-emitting elements may surround each of the plurality of light-receiving elements.

The light-receiving element and the plurality of light-emitting elements surrounding the light-receiving element form a first sub unit, and a plurality of sub units including the first sub unit are repetitively arranged in the form of a hive.

The analyzing unit may be further configured to measure a time delay between the at least two points and calculate a pulse transit time (PTT) from the time delay.

The analyzing unit may be further configured to analyze vessel elasticity, blood flow rate, arterial stiffness, and systolic blood pressure or diastolic blood pressure of a vessel, from the PTT.

The light-emitting element may include a light-emitting diode (LED) or a laser diode, and the light-receiving element may include a photodiode, a photo transistor (PTr), or a charge-coupled device (CCD).

The apparatus may further include a user interface configured to output a result regarding the analyzed biometric information.

The apparatus may include a communicator transmitting a result regarding the analyzed biometric information to an external device.

The biometric signal measurer may be wearable by the object.

The apparatus may be wearable by the object.

According to an aspect of another exemplary embodiment, there is provided a radial artery tracking method including: sequentially driving a plurality of light-emitting elements and radiating light from the plurality of light-emitting elements to an object, detecting optical signals through a light-receiving element according to the sequential driving of the plurality of light-emitting elements, determining, by a processor, at least two highest level signals among the detected optical signals, and determining, by the processor, a line connecting positions of at least two light-emitting elements corresponding to the determined at least two highest level signals as a tracking line.

According to an aspect of another exemplary embodiment, there is provided a method of detecting biometric information of an object including: sequentially driving a plurality of light-emitting elements and radiating light from the plurality of light-emitting elements to the object, detecting optical signals through a light-receiving element according to the sequential driving of the plurality of light-emitting elements, measuring a time delay between two or more highest level signals among the detected signals; and analyzing biometric information based on the measured time delay.

The biometric information may include vessel elasticity, blood flow rate, arterial stiffness, and systolic blood pressure or diastolic blood pressure of a vessel.

According to an aspect of another exemplary embodiment, there is provided a biometric signal measurer including: a plurality of light emitting elements configured to sequentially turn on and off and radiate light to a target area on a skin of a subject to deflect the radiated light from the target area; and at least one optical sensor configured to detect the deflected light and disposed at a center position of a perimeter formed by connecting the plurality of light emitting elements; wherein while one of the plurality of light emitting elements is turned on, remaining ones of the plurality of light stay turned off.

Wherein the plurality of light emitting elements are classified into as belonging to a least one of a first unit, a second unit, and a third unit, the at least one optical sensor includes a first optical sensor belonging to the first unit, a second optical sensor belonging to the second unit, and a third optical sensor belonging to the third unit, and the first, second, and third units are arranged in a form of a hive.

The first, second, and third units are sequentially controlled to turn on and off the plurality of light emitting elements sequentially.

At least one of the plurality of light emitting elements belongs to the first unit and the second unit and at least another one of the plurality of light belongs to the first unit and the third unit.

BRIEF DESCRIPTION OF THE DRAWINGS

The above and/or other aspects will be more apparent by certain exemplary embodiments, with reference to the accompanying drawings, in which:

FIG. 4 is a flowchart illustrating a radial artery tracking method executed by an apparatus for detecting biometric information according to an exemplary embodiment;

DETAILED DESCRIPTION

Figure 1:
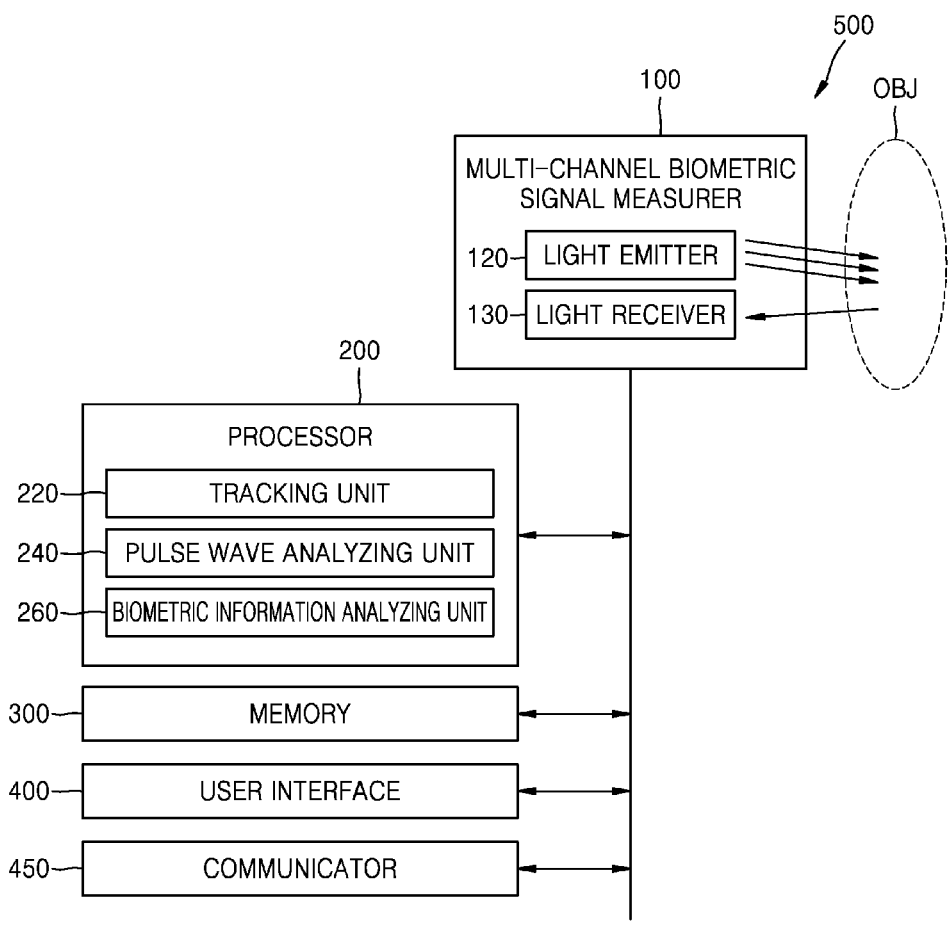
FIG. 1 is a block diagram illustrating a schematic structure of an apparatus for detecting biometric information according to an exemplary embodiment.

Exemplary embodiments are described in greater detail below with reference to the accompanying drawings.

The matters defined in the description, such as detailed construction and elements, are provided to assist in a comprehensive understanding of the exemplary embodiments. However, it is apparent that the exemplary embodiments can be practiced without those specifically defined matters. Also, well-known functions or constructions are not described in detail since they would obscure the description with unnecessary detail.

As used herein, the term "and/or" includes any and all combinations of one or more of the associated listed items. Expressions such as "at least one of," when preceding a list of elements, modify the entire list of elements and do not modify the individual elements of the list.

Throughout the drawings, like reference numerals refer to like elements, and the size of each element may be exaggerated for clarity and convenience.

In the following description, when a layer, region, or component is referred to as being "above" or "on" another layer, region, or component, it can be directly or indirectly on the other layer, region, or component.

In the following embodiments, terms such as "first", "second", and so forth are used only for distinguishing one component from another component, rather than for restrictive meanings.

In the following embodiments, the terms "comprises" and/or "has" when used in this specification, specify the presence of stated feature, number, step, operation, component, element, or a combination thereof but do not preclude the presence or addition of one or more other features, numbers, steps, operations, components, elements, or combinations thereof.

Terms used herein, such as "unit" and "module" refer to a unit for processing at least one functions or operations, and may be implemented with hardware (e.g., a processor or circuit), software, or a combination thereof.

Figure 2:
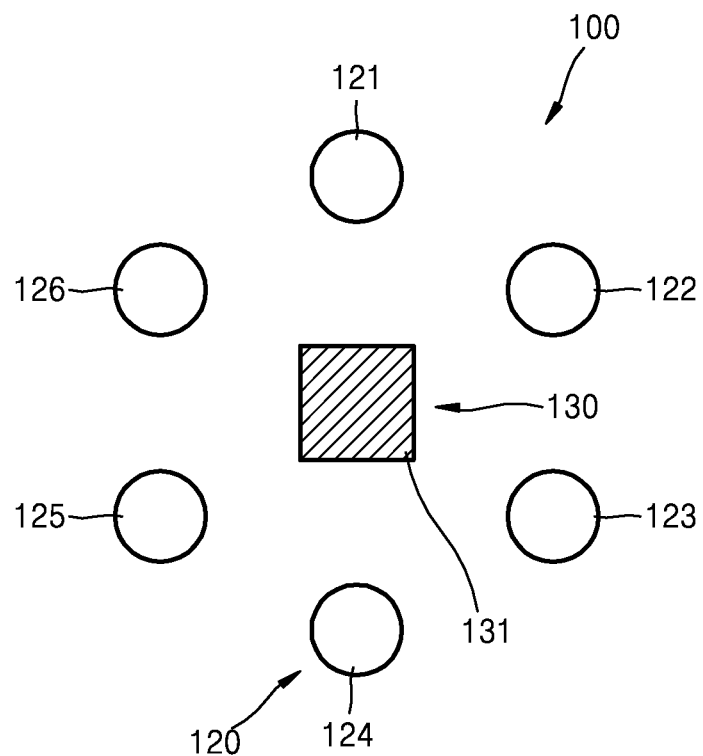
FIG. 2 is a planar view illustrating arrangement of light-emitting elements and a light-receiving element of a multi-channel biometric signal measurer used in an apparatus for detecting biometric information according to an exemplary embodiment.

FIG. 1 is a block diagram illustrating a schematic structure of an apparatus for detecting biometric information (or a biometric information detection apparatus) 500 according to an exemplary embodiment, and FIG. 2 is a planar view illustrating arrangement of light-emitting elements and a light-receiving element of a multi-channel biometric signal measurer 100 used in the biometric information detection apparatus 500 according to an exemplary embodiment.

The biometric information detection apparatus 500 detects biometric information of an object OBJ. The biometric information detection apparatus 500 includes the multi-channel biometric signal measurer 100 and a processor 200 that controls the multi-channel biometric signal measurer 100 and performs biometric information analysis based on a measurement result. The biometric information detection apparatus 500 may further include a memory 300 and a user interface 400.

The multi-channel biometric signal measurer 100 may include a light emitter 120 and a light receiver (also referred to as "optical sensor") 130. The light emitter 120 radiates light to the object OBJ, and the light receiver 130 detects light scattered or reflected from the object OBJ. The detected optical signal is used variously for biometric information analysis, as will be described in detail.

The object OBJ is a target for biometric information detection, and may be a biologic part that may contact or may be adjacent to the multi-channel biometric signal measurer 100 of the biometric information detection apparatus 500, or may be a body part for which pulse wave measurement is easy to perform through photoplethysmography (PPG). PPG is an optical technique to detect blood volume changes of a vessel by illuminating the skin above the vessel and measuring changes in light of absorption. The object OBJ may be a part that is adjacent to a radial artery in a wrist. When a pulse wave is measured on the surface of the skin of the wrist through which a radial artery passes, an influence of external factors causing an error of measurement of, for example, the thickness of a skin tissue inside the wrist may be small. The radial artery is known as a blood vessel for which the more accurate blood pressure may be measured than other types of blood vessels in the wrist. However, the object OBJ is not limited to these examples, and may be a terminal part of a human body, such as a finger, a toe, or an earlobe, in which vessel density is high.

As shown in FIG. 2, the light emitter 120 of the multi-channel biometric signal measurer 100 may include a plurality of light-emitting elements 121 through 126, and the light receiver 130 may include a light-receiving element 131. The plurality of light-emitting elements 121 through 126 may be arranged to surround the light-receiving element 131. Although six light-emitting elements, that is, first through sixth light-emitting elements 121-126 are arranged isotropically around the light-receiving element 131 in FIG. 2, the present disclosure is not limited to that example.

Light-emitting diodes (LEDs) or laser diodes may be used as the first through sixth light-emitting elements 121 through 126. The first through sixth light-emitting elements 121 through 126 are sequentially driven one by one and may radiate light to the object OBJ.

The light receiver 130 may be a photodiode, a photo transistor (PTr), or a charge-coupled device (CCD). The light-receiving element 131 senses an optical signal scattered or reflected from the object OBJ. For example, a laser speckle generated by scattering of laser light radiated to the object OBJ may be detected. The laser speckle means an irregular pattern generated by interference or scattering when a laser having coherency is radiated to a scattering object. The light-receiving unit 130 detects an optical signal corresponding to the laser speckle.

The processor 200 may include a tracking unit 220, a pulse wave analyzing unit 240, and a biometric information analyzing unit 260.

The tracking unit 220 sequentially drives the plurality of light-emitting elements 121 through 126 included in the multi-channel biometric signal measurer 100, senses a signal detected by the light-receiving unit 130, and tracks a position of a radial artery of the object OBJ from the sensed signal. More specifically, when the multi-channel biometric signal measurer 100 radiates light and detects an optical signal in contact with or in adjacent to the object OBJ, a signal-to-noise ratio of the detected optical signal varies with a relative position of the plurality of light-emitting elements 121 through 126 with respect to a radial artery of the object OBJ. For example, when among the plurality of light-emitting elements 121 through 126, a light-emitting element that is close to a radial artery radiates light, an optical signal detected by the light receiver 130 has a high signal-to-noise ratio, and when a light-emitting element that is far from the radial artery radiates light, an optical signal detected by the light receiver 130 has much noise and thus a low signal-to-noise ratio. As such, by analyzing a signal-to-noise ratio of a detected optical signal, at least two light-emitting elements may be selected, and a line connecting positions of the light-emitting elements may be determined as a radial artery tracking line.

The pulse wave analyzing unit 240 analyzes a pulse wave signal at at least two points on a tracking line determined by the tracking unit 220. More specifically, the pulse wave analyzing unit 240 analyzes a time-specific strength change of an optical signal detected by the light receiver 130. The pulse wave analyzing unit 240 may obtain a biometric signal by analyzing fluctuation of a laser speckle corresponding to a volume change of a vessel (for example, a radial artery) of the object OBJ. Herein, the obtained biometric signal may be a PPG signal converted based on a correlation between the analyzed fluctuation of the laser speckle and the volume change. The pulse wave analyzing unit 240 analyzes various parameters included in the PPG signal by analyzing waveform characteristics of the PPG signal. For example, the pulse wave analyzing unit 240 may calculate a delay time between pulse wave signals and calculate a pulse transit time (PTT). In this process, the pulse wave analyzing unit 240 may use various digital signal processing algorithms such as a noise cancellation algorithm, a differential signal extraction algorithm, and so forth.

The biometric information analyzing unit 260 analyzes various biometric information by using a pulse wave signal analysis result as an index. The biometric information analyzing unit 260 may analyze biometric information by using a predetermined algorithm for calculating various biometric information from the PTT calculated by the pulse wave analyzing unit 240. For example, vessel elasticity, blood flow rate, arterial stiffness, systolic blood pressure of a vessel, diastolic blood pressure, or the like may be estimated.

The memory 300 stores a program for processing and controlling the processor 200 and stores input/output data. For example, a program for the tracking, the pulse wave analysis, and the biometric information analysis performed in the processor 200 may be stored as a code in the memory 300. Measurement results of the multi-channel biometric signal measurer 100, which are necessary for processing in the processor 200, may be stored in the memory 300.

The memory 300 may include storage media of at least one type of a flash memory type, a hard disk type, a multimedia card micro type, a card type (for example, a secure digital (SD) or extreme digital (XD)), a random access memory (RAM) type, a static random access memory (SRAM) type, a read-only memory (ROM) type, an electrically erasable programmable read-only memory (EEPROM) type, a programmable read-only memory (PROM) type, a magnetic memory type, a magnetic disk type, an optical disk type, and so forth.

The user interface 400 is an interface with a user and/or an external device, and may include an input unit and an output unit. Herein, the user may be a target for measurement of biometric information, that is, the object OBJ, but may also be a person who may use the biometric information detection apparatus 500, such as a medical expert, so that the user may be a broader concept than the object OBJ. Through the user interface 400, information necessary for operating the biometric information detection apparatus 500 may be input, and an analysis result may be output. The user interface may include, for example, a button, a connector, a keypad, a display unit, and the like, and may further include an audio output unit, a vibration motor, and so forth.

The biometric information detection apparatus 500 may further include a communicator 450 for transmitting an analysis result to an external device. The external device may be medical equipment using analyzed biometric information, a printer for printing a result, or a display device for displaying an analysis result. The external device may also be, but not limited to, a smart phone, a cellular phone, a personal digital assistant (PDA), a laptop, a personal computer (PC), or other mobile or non-mobile computing devices.

The communicator 450 may include a transmitter, a receiver, or a transceiver. The communicator 450 may be connected with the external device in a wired or wireless manner. For example, the communicator 450 may communicate with the external device by using, but not limited to, Bluetooth communication, Bluetooth low energy (BLE) communication, near field communication (NFC), wireless local area network (WLAN) communication, ZigBee communication, infrared data association (IrDA) communication, wireless fidelity direct (WFD) communication, ultra wideband (UWB) communication, Ant+ communication, Wi-Fi communication, or the like.

The biometric information detection apparatus 500 may be implemented in a wearable device that may be worn on the object OBJ. For example, the biometric information detection apparatus 500 may be implemented in the form of, but not limited to, a wrist watch, a bracelet, a wrist band, a ring, glasses, a hairband, or the like.

Alternatively, only a portion of the biometric information detection apparatus 500, for example, the multi-channel biometric signal measurer 100 may be implemented in a form that is wearable on the object OBJ as illustrated.

Figure 3A:
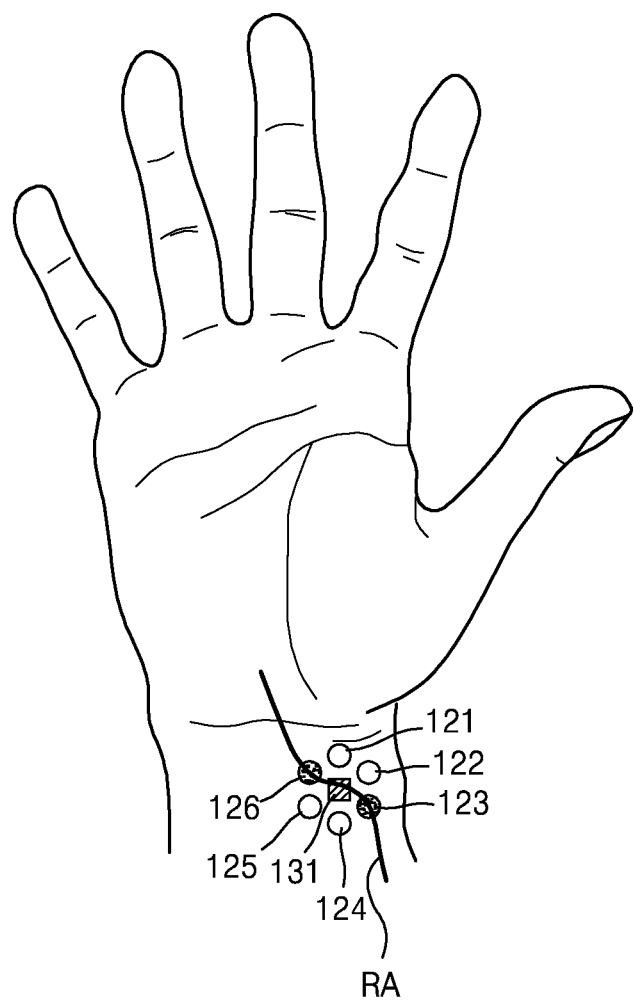
FIGS. 3A through 3C illustrate selective activation of some light-emitting elements of a multi-channel biometric signal measurer based on different radial arteries for different persons according to an exemplary embodiment.
Figure 3B:
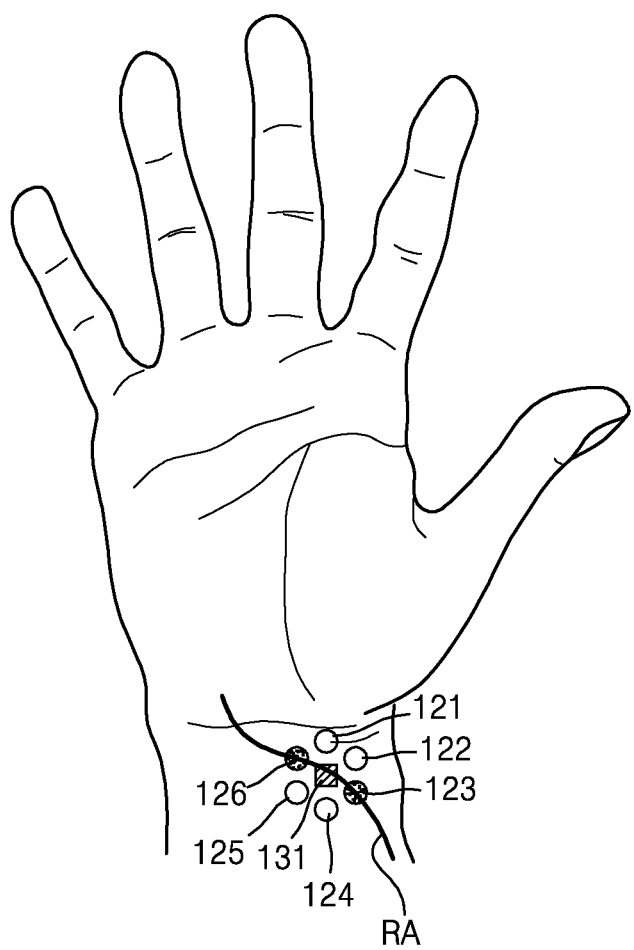
Figure 3C:
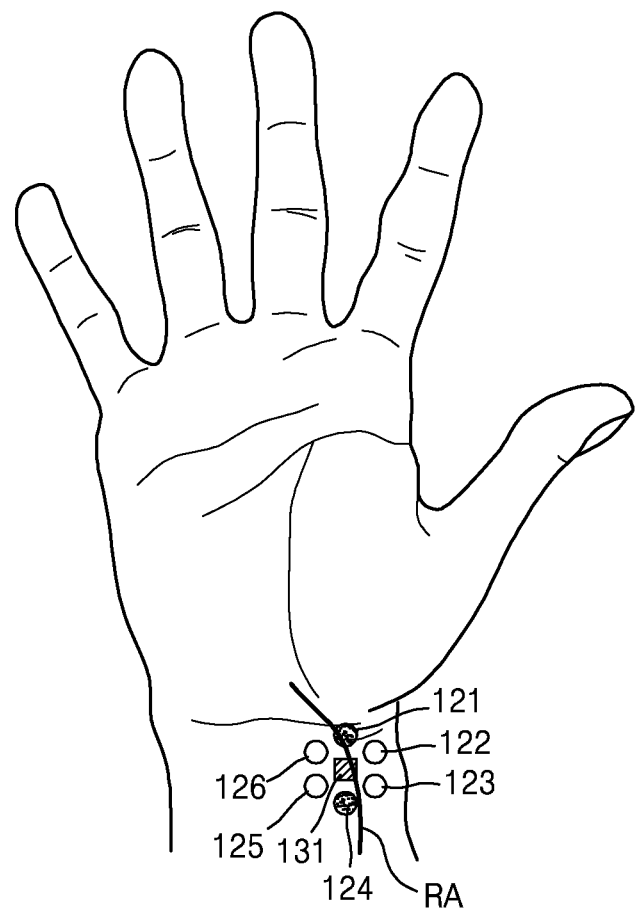

FIGS. 3A through 3C illustrate selective activation of some light-emitting elements of the multi-channel biometric signal measurer 100 according to a radial artery pattern that differs from person to person.

FIG. 3A shows that a third light-emitting element 123 and a sixth light-emitting element 126, which are closest onto a radial artery RA, are activated. FIG. 3B shows that the third light-emitting element 123 and the sixth light-emitting element 126, which are closest onto the radial artery RA, are activated. Referring to FIG. 3C, a first light-emitting element 121 and a fourth light-emitting element 124, which are closest onto the radial artery RA, are activated.

FIGS. 3A through 3C illustrate an example in which a radial artery pattern varying from person to person is tracked according to a tracking result obtained from the multi-channel biometric signal measurer 100. In pulse wave signal detection, the plurality of light-emitting elements indicated as being activated are driven one by one and an optical signal is detected. However, the present embodiment is not limited thereto, such that the plurality of light-emitting elements indicated as being activated may also be driven at the same time and an optical signal may be detected.

FIG. 4 is a flowchart illustrating a radial artery tracking method executed by the biometric information detection apparatus 500 according to an exemplary embodiment. FIGS. 5A through 5E illustrate activation of some light-emitting elements of the multi-channel biometric signal measurer 100 when radial artery tracking is performed by the biometric information detection apparatus 500 according to an exemplary embodiment. FIG. 6 illustrates an example of tracking a radial artery from a detection signal in driving illustrated in FIGS. 5A through 5E.

As shown in FIG. 4, light radiation, optical signal detection in a light-receiving element, and identification and storage of a signal level of a pulse wave (operations S201 through S204) are repeated as many times as the number of channels, that is, the number of light-emitting elements.

Figure 5A:
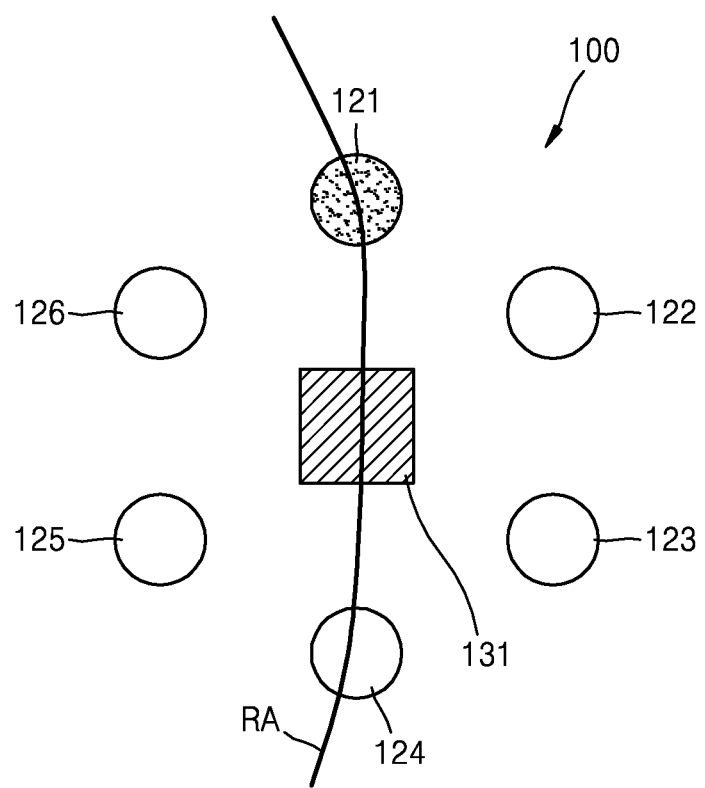
FIGS. 5A through 5E illustrate activation of some light-emitting elements of a multi-channel biometric signal measurer when radial artery tracking is performed by an apparatus for detecting biometric information according to an exemplary embodiment.
Figure 6:
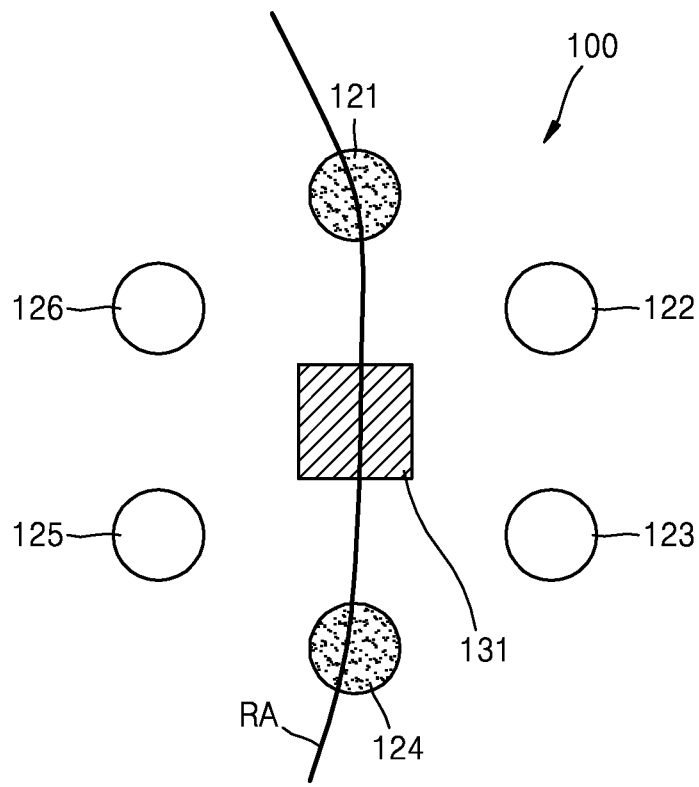
FIG. 6 illustrates an example of tracking a radial artery from a detection signal in driving illustrated in FIGS. 5A through 5E.

First, as illustrated in FIG. 5A, when the first light-emitting element 121 is driven and the other light-emitting elements 122 through 126 are turned off, the light-receiving element 131 detects an optical signal in operation S202.

The detected optical signal may include a strength change over time in connection with a volume change of a radial artery, as descried before. A pulse wave is analyzed from the detected signal, and a signal level of the pulse wave is identified and stored as an index for use in radial artery tracking in operation S203. The signal level of the pulse wave may include information such as a signal-to-noise ratio.

Next, as illustrated in FIGS. 5B through 5E, when second light-emitting elements 122 through sixth light-emitting elements 126 are driven and the other light-emitting elements are turned off, the light-receiving element 131 detects an optical signal in operation S202, and identifies and stores a signal level of a pulse wave in operation S203.

The stored results are compared to select two optimal points, and a tracking line is determined in operation S204. The two optimal points may be selected in a descending order of a signal-to-noise ratio. For example, a light-emitting element corresponding to the highest signal-to-noise ratio and a light-emitting element corresponding to the next highest signal-to-noise ratio may be selected, and a line connecting two positions may be determined as a tracking line.

Figure 5B:
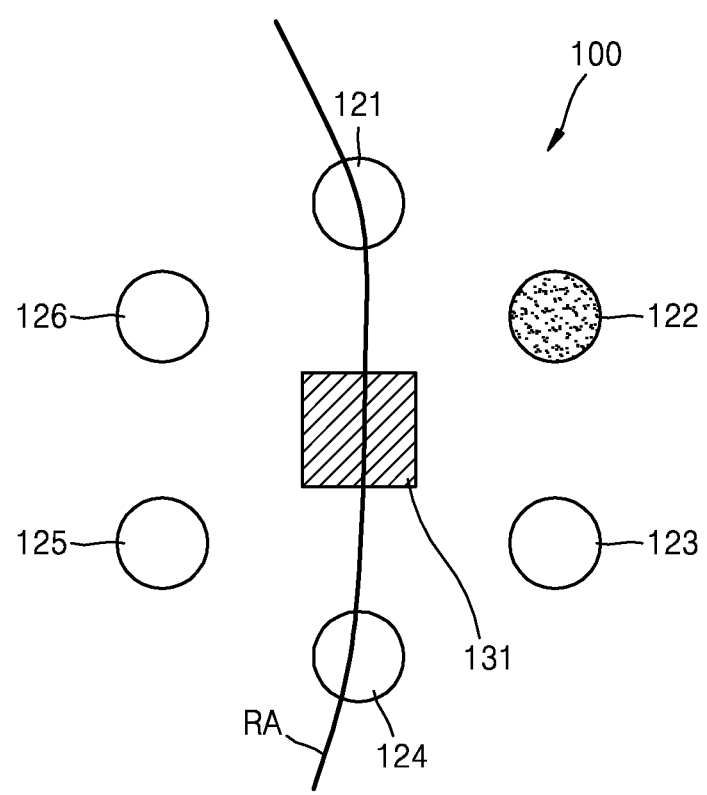
Figure 5C:
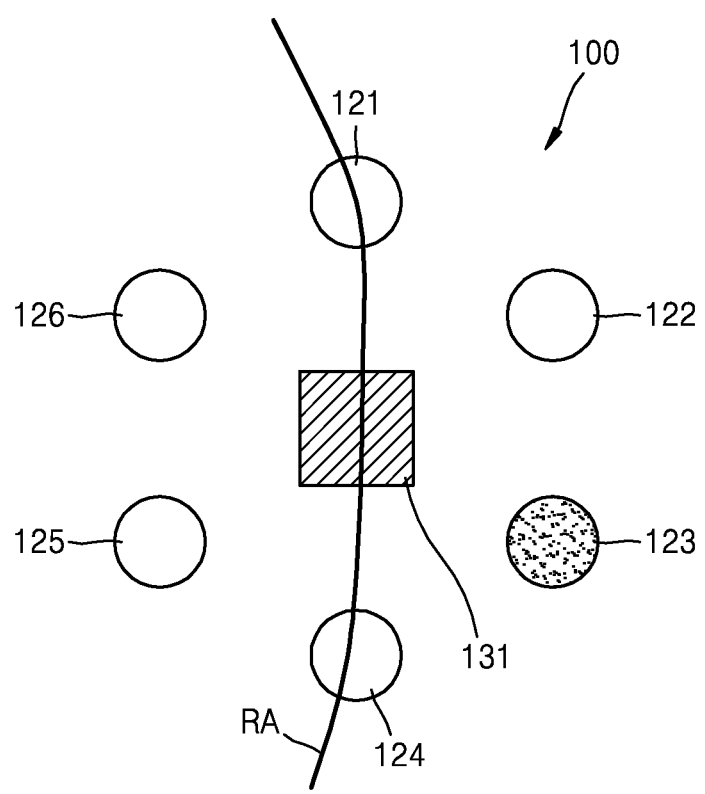
Figure 5D:
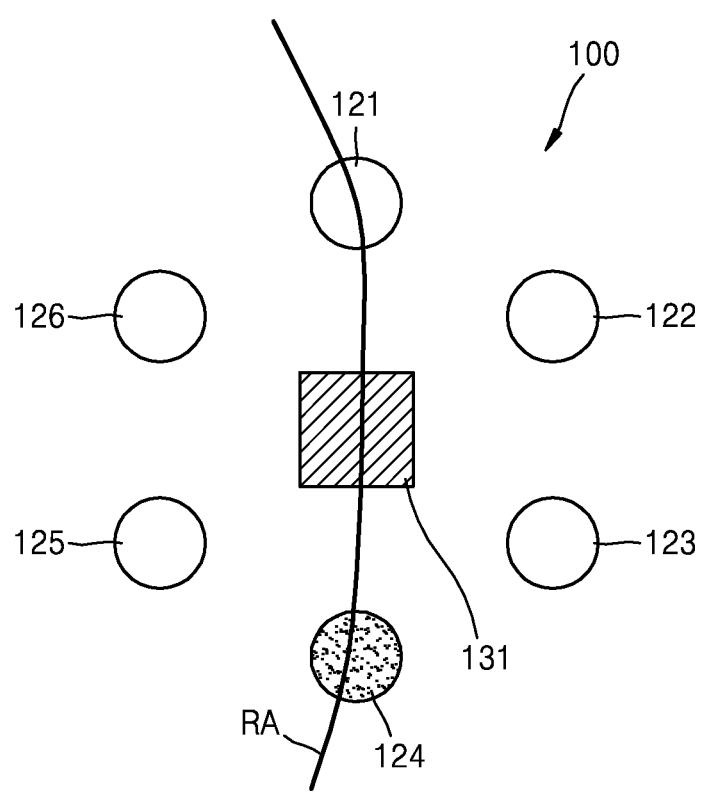
Figure 5E:
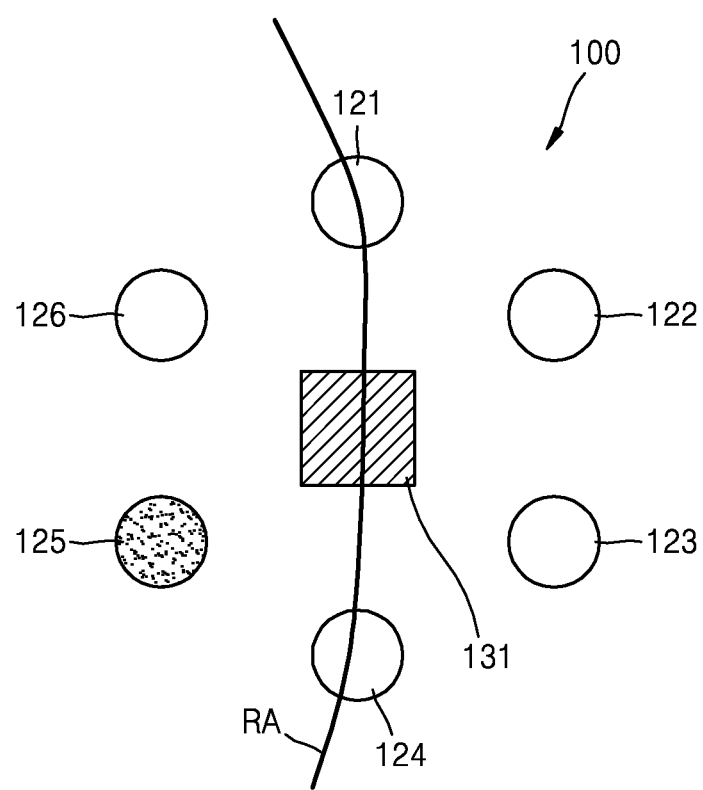

Since the first light-emitting element 121 and the fourth light-emitting element 124 are located on the surface of the skin above the radial artery AR, the optical signal detected by the light-receiving element 131 has a higher signal-to-noise ratio when the first light-emitting element 121 or the fourth light-emitting element 124 is turned on as shown in FIGS. 5A and 5B than when one of the second, third, and sixth light-emitting elements 122, 123, and 126 is turned on as shown in FIGS. 5B, 5C, and 5E. That is, as illustrated in FIG. 6, a line connecting the positions of the first light-emitting element 121 and the fourth light-emitting element 124 may be determined as a radial artery tracking line.

Although it has been described that two light-emitting elements are disposed at positions facing a radial artery, the present embodiment is not limited thereto and various cases may exist. For example, one light-emitting element may face the radial artery and the other light-emitting element may be disposed in adjacent to the light-emitting element. In this case, the highest signal-to-noise ratio is clearly seen, but the second and third highest signal-to-noise ratios may be slightly different. In this case, a position of a light-emitting element corresponding to the highest signal-to-noise ratio is determined as a first optimal point, and an intermediate point between light-emitting elements corresponding to the second and third highest signal-to-noise ratios may be determined as a second optimal point.

Figure 7:
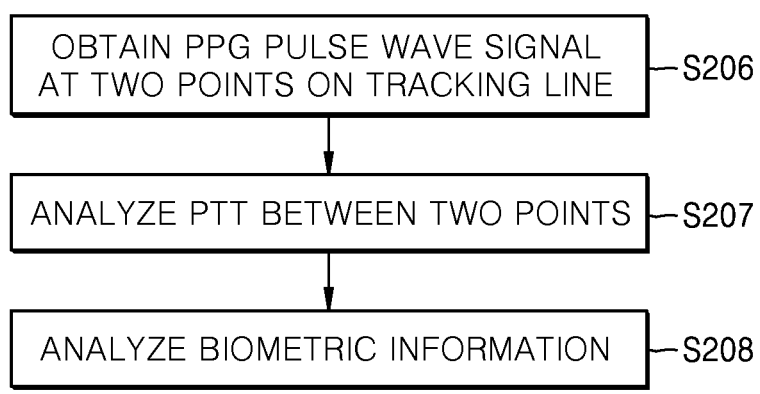
FIG. 7 is a flowchart illustrating a process of analyzing biometric information after tracking a radial artery in an apparatus for detecting biometric information according to an exemplary embodiment.
Figure 8:
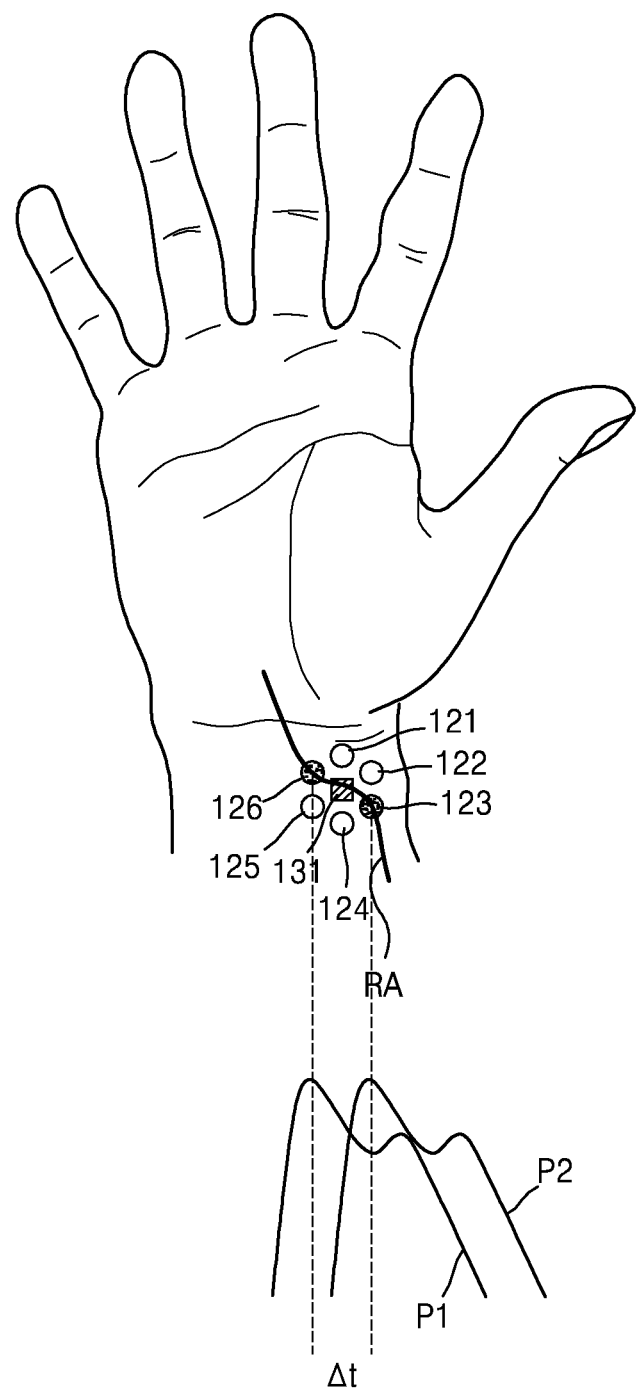
FIG. 8 illustrates a signal pattern detected at a plurality of points on a tracked radial artery.

FIG. 7 is a flowchart illustrating a process of analyzing biometric information after tracking a radial artery in the biometric information detection apparatus 500 according to an exemplary embodiment. FIG. 8 illustrates a signal pattern detected at a plurality of points on a tracked radial artery.

Once a radial artery tracking line is determined, a PPG pulse wave signal at two points on the tracking line is obtained in operation S206. These two points may be the two optimal points determined in FIGS. 4 and 5A through 5E. Thus, light may be radiated to corresponding positions and optical signal detection and pulse wave analysis may be performed. The results stored in operation S203 of FIG. 4 may also be used.

Next, a PTT is analyzed from two pulse wave signals in operation S207.

As illustrated in FIG. 8, by comparing waveforms of two obtained pulse wave signals P1 and P2, a time delay $\Delta t$ is analyzed. The time delay $\Delta t$ is a parameter related to PTT information, from which the PTT may be analyzed.

Next, by using the pulse wave signal waveform information and the PTT information, biometric information may be analyzed in operation S208. The biometric information may include vessel elasticity, blood flow rate, arterial stiffness, systolic blood pressure, diastolic blood pressure, or information indicating whether a current blood pressure state is a normal state or an abnormal state.

Figure 9:
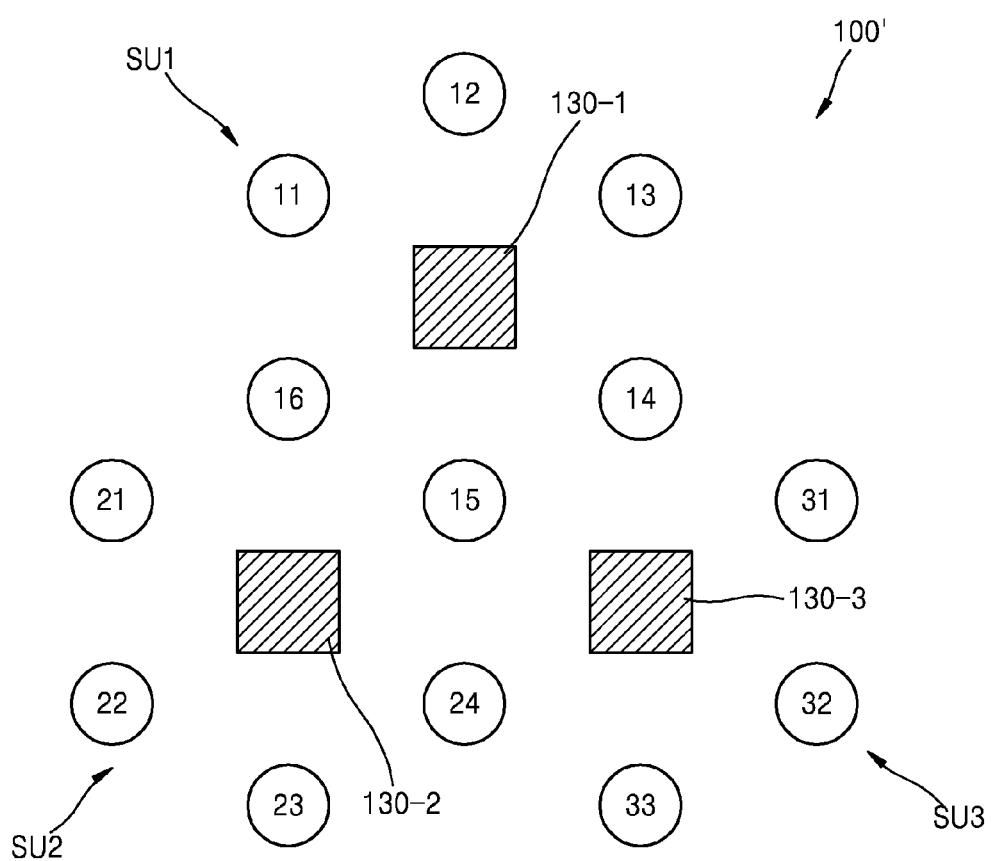
FIG. 9 illustrates arrangement of light-emitting elements and a light-receiving element of a multi-channel biometric signal measurer used in an apparatus for detecting biometric information according to another exemplary embodiment.

FIG. 9 illustrates arrangement of light-emitting elements and a light-receiving element of a multi-channel biometric signal measurer 100' used in an apparatus for detecting biometric information according to another exemplary embodiment.

The multi-channel biometric signal measurer 100' may include a plurality of light-receiving elements and a plurality of light-emitting elements disposed to surround each of the plurality of light-receiving elements.

More specifically, a first light-receiving element 130_1 and a plurality of light-emitting elements 11 through 16 surrounding the first light-receiving element 130_1 form a first sub unit SU1. A second light-receiving element 130_2 and a plurality of light-emitting elements 21 through 24, 15, and 16 surrounding the second light-receiving element 130_2 form a second sub unit SU2. A third light-receiving element 130_3 and a plurality of light-emitting elements 31 through 33, 25, 15, and 14 surrounding the third light-receiving element 130_3 form a third sub unit SU3.

Figure 10:
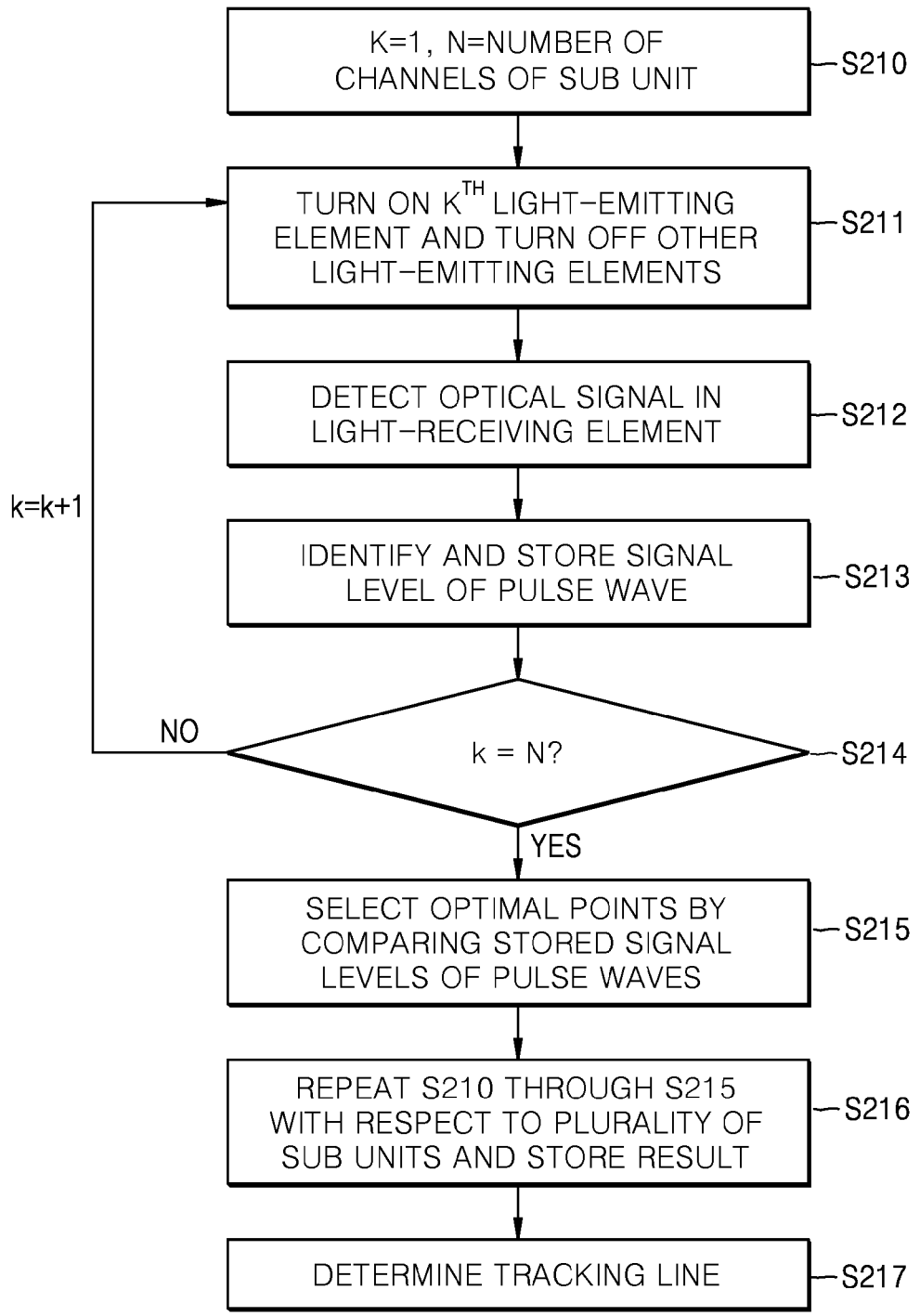
FIG. 10 is a flowchart illustrating a radial artery tracking method executed in an apparatus for detecting biometric information including a multi-channel biometric signal measurer of FIG. 9.

FIG. 10 is a flowchart illustrating a radial artery tracking method executed in an apparatus for detecting biometric information including the multi-channel biometric signal measurer 100' of FIG. 9.

For one sub unit, when a plurality of light-emitting elements included in one sub unit are sequentially selected and driven one by one and the other light-emitting elements are turned off in operation S211, a light-receiving element detects an optical signal in operation S212 and a signal level of a pulse wave is identified and stored in operation S213. After the foregoing processes are also done with respect to all the light-emitting elements included in the sub unit, stored pulse wave signal levels are compared to select an optimal point in operation S215. At this time, the selected optimal point may be one or more points, or zero (0) point. In the current embodiment, the foregoing measurement is repeated with respect to the plurality of sub units, such that two or more optimal points are selected eventually and for some sub units, an optimal point may not be selected. For example, for some sub units, a signal-to-noise ratio in every channel is very low and thus a signal-to-noise ratio difference is not meaningful, and in this case, an optimal point may not be selected.

Operations S210 through S215 are repeated with respect to a plurality of sub units, that is, first through third sub units SU1, SU2, and SU3 and results are stored in operation S216. A tracking line is determined from an optimal point determined in measurement with respect to each sub unit in operation S217. The tracking line may be determined by two or more optimal points, and in this case, for example, some of the optimal points selected in operation S215 may not be reflected in a finally determined tracking line. For the determination, a connection relationship between the optimal points selected in measurement with respect to each of the plurality of sub units or a total signal-to-noise ratio level of a channel may be considered.

When operations S210 through S215 are repeated with respect to the first, second, and third sub units SU1, SU2, and SU3, the light-emitting elements 14, 15, 16, and 24 which belong to two or three of the sub units SU1, SU2, and SU3 may be set to be turned on once and optical signals of the light-emitting elements 14, 15, 16, and 24 may be measured once. For example, if the first unit SU1 performs operations S210-S214 prior to the second unit SU2 and the third unit SU3, the first unit SU1 may perform operations S211-S213 for all of its light-emitting elements 12-16 but the second unit SU2 may perform operations S211-S213 only for the light-emitting elements 21-24 and skip operations S211-S213 with respect to the light-emitting elements 15 and 16. Further, the third unit SU3 may perform operations S211-S213 only for the light-emitting elements 31-33 and skip operations S211-S213 with respect to the light-emitting elements 14, 15, and 24. In that case, two or more optimal points may be selected from the light emitting elements 11-16, 21-24, and 31-33 regardless of the sub units SU1, SU2, and SU3 which the light emitting elements 11-16, 21-24, and 31-33 belong to. For example, if four optimal points are set to be selected and pulse wave signal levels measured from the light emitting elements 11, 15, 24, and 33 are higher than the other light emitting elements 12-14, 21-23, and 31-32, a line connecting the light emitting elements 11, 15, 24, and 33 may be determined as a tracking line in operation S217.

Figure 11:
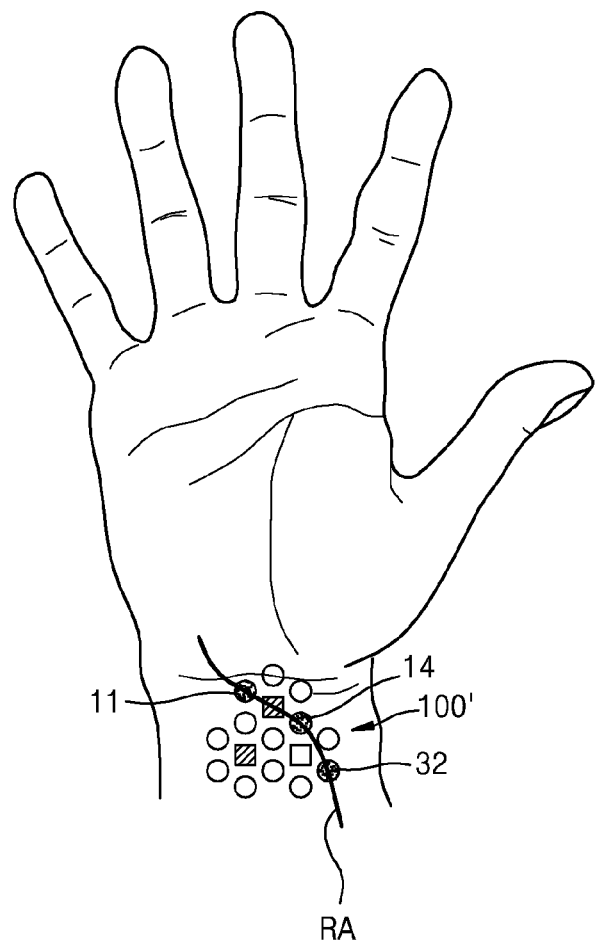
FIG. 11 illustrates activation of some light-emitting elements according to a radial artery pattern tracked using the flowchart illustrated in FIG. 10.

FIG. 11 illustrates activation of some light-emitting elements according to a radial artery pattern tracked using the flowchart illustrated in FIG. 10.

FIG. 11 shows determining a track line based on positions of the light-emitting elements 11, 14, and 32.

Figure 12:
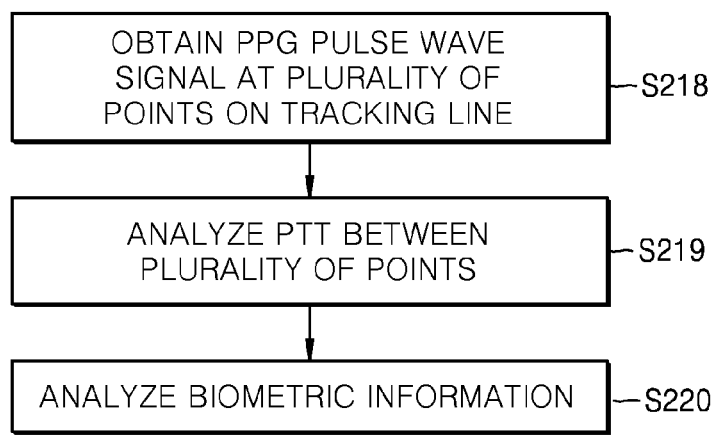
FIG. 12 is a flowchart illustrating a process of analyzing biometric information after tracking a radial artery in an apparatus for detecting biometric information according to another exemplary embodiment.
Figure 13:
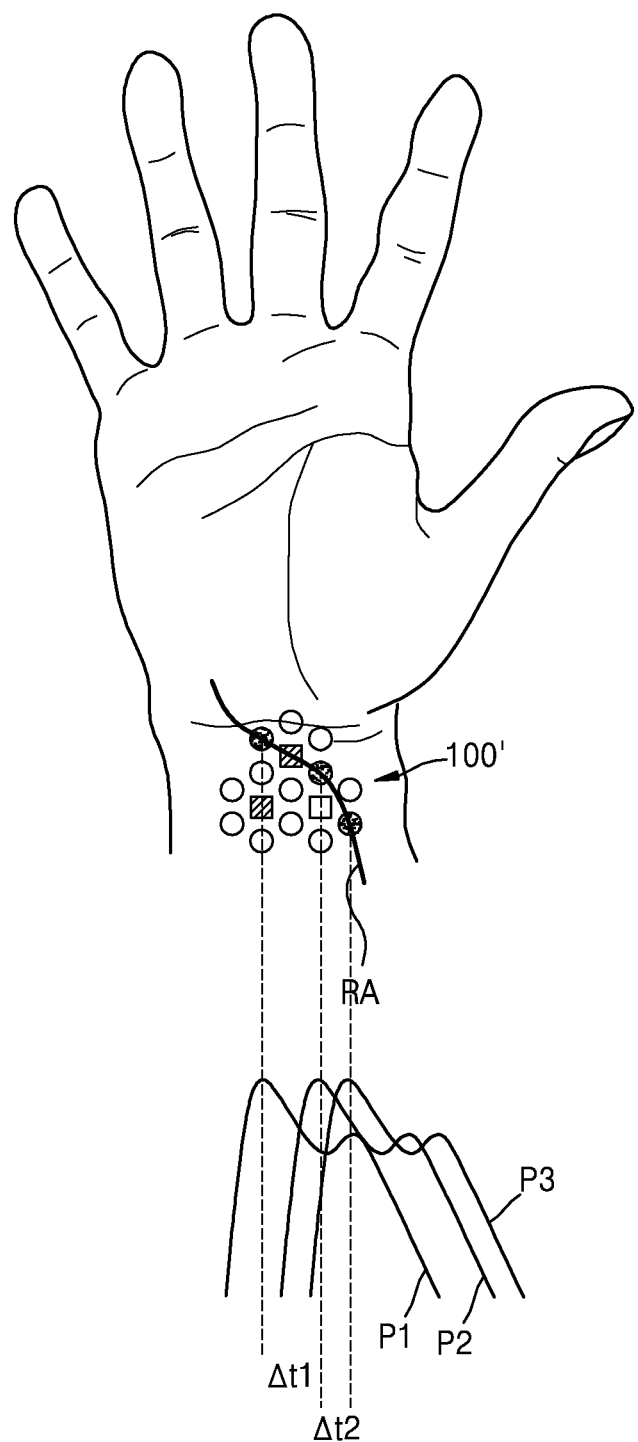
FIG. 13 illustrates a signal pattern detected at a plurality of points on a tracked radial artery.

FIG. 12 is a flowchart illustrating a process of analyzing biometric information after tracking a radial artery by using the multi-channel biometric signal measurer 100' of FIG. 9 in an apparatus for detecting biometric information according to another exemplary embodiment, and FIG. 13 illustrates a signal pattern detected by a plurality of points on a tracked radial artery.

Once the radial artery tracking line is determined, a PPG pulse wave signal at a plurality of points on the tracking line is obtained in operation S218. The two points may be two or more optimal points determined in FIG. 10. For example, as illustrated in FIG. 11, three points may be used. Light is radiated to corresponding positions, and a PPG pulse wave signal may be obtained by performing optical signal detection and pulse wave analysis. The result stored in operation S213 of FIG. 10 may be used.

Next, a PTT is analyzed from a plurality of pulse wave signals in operation S219.

As illustrated in FIG. 13, waveforms of three obtained pulse wave signals P1, P2, and P3 are compared to analyze time delays Δt1 and Δt1. The time delays Δt1 and Δt1 are parameters related to PTT information, from which the PTT may be analyzed.

Next, biometric information is analyzed by using pulse wave signal waveform information, PTT information, and so forth in operation S220. The biometric information may include vessel elasticity, blood flow rate, arterial stiffness, systolic blood pressure, diastolic blood pressure, or information indicating whether a current blood pressure state is a normal state or an abnormal state.

In the foregoing description, the multi-channel biometric signal measurer 100 of FIG. 9 includes three sub units, but the multi-channel biometric signal measurer 100 may three or more sub units.

Figure 14:
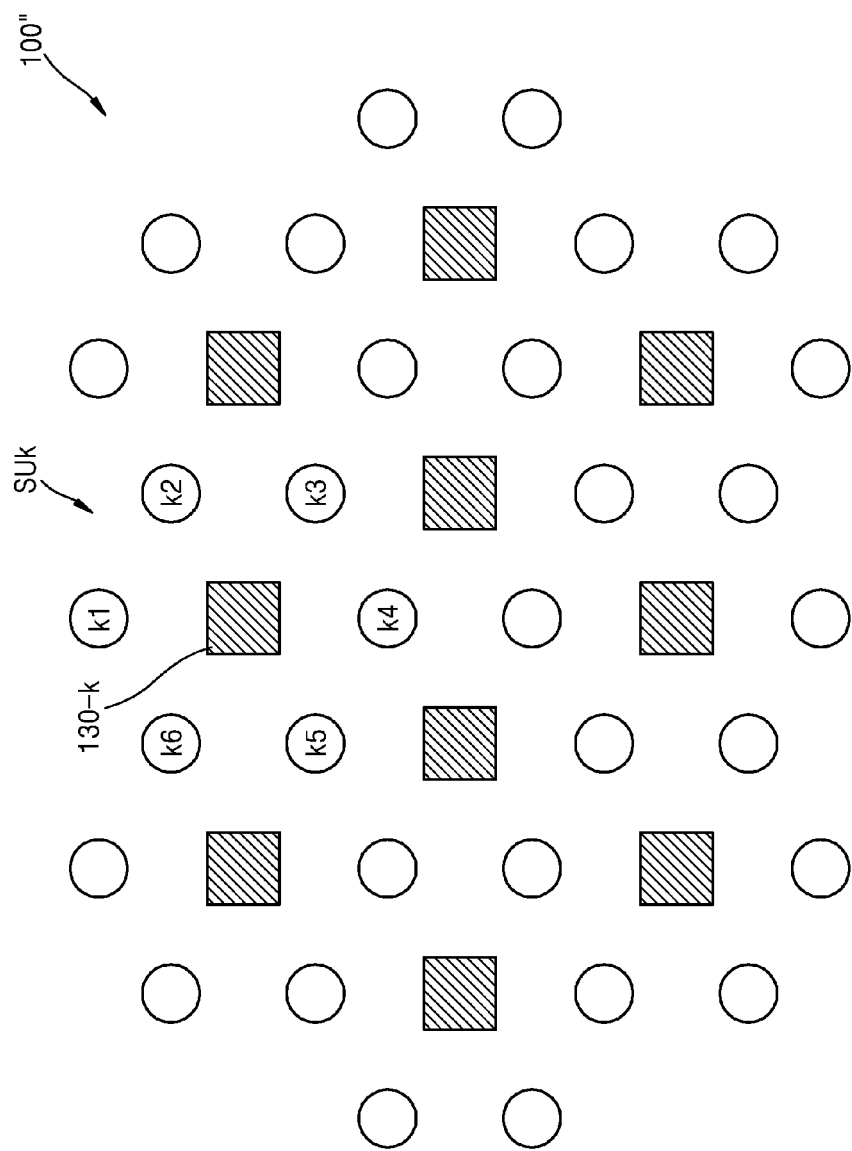
FIG. 14 illustrates arrangement of light-emitting elements and a light-receiving element of a multi-channel biometric signal measurer used in an apparatus for detecting biometric information according to another exemplary embodiment.

FIG. 14 illustrates arrangement of light-emitting elements and a light-receiving element of a multi-channel biometric signal measurer 100" used in an apparatus for detecting biometric information according to another exemplary embodiment.

In the current embodiment, the multi-channel biometric signal measurer 100" is configured such that a plurality of sub units SUk, each of which includes a light-receiving element 130_k and a plurality of light-emitting elements k1 through k6 surrounding the light-receiving element 130_k, are arranged in the form of a hive. Driving of the biometric information detection apparatus including the multi-channel biometric signal measurer 100″ is substantially the same as the foregoing description.

As the number of sub units SUk increases, the accuracy of radial artery tracking line analysis and the accuracy of pulse wave analysis and biometric information analysis based thereon may increase.

As described above, using the apparatus and method for detecting biometric information according to the one or more of the above exemplary embodiments, radial artery tracking is possible according to a radial artery pattern varying from person to person.

In addition, by using a pulse wave signal at a plurality of tracked points, various biometric information may be analyzed.

The computer readable code can be recorded/transferred on a medium in a variety of ways, with examples of the medium including recording media, such as magnetic storage media (e.g., ROM, floppy disks, hard disks, etc.) and optical recording media (e.g., CD-ROMs, or DVDs), and transmission media such as Internet transmission media. Thus, the medium may be such a defined and measurable structure including or carrying a signal or information, such as a device carrying a bitstream according to one or more exemplary embodiments. The media may also be a distributed network, so that the computer readable code is stored/transferred and executed in a distributed fashion. Furthermore, the processing element could include a processor or a computer processor, and processing elements may be distributed and/or included in a single device.

The foregoing exemplary embodiments and advantages are merely exemplary and are not to be construed as limiting. The present teaching can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. An apparatus for detecting biometric information of an object, the apparatus comprising:
    a biometric signal measurer comprising a first light-receiving element, a plurality of first light-emitting elements, a second light-receiving element, and a plurality of second light-emitting elements, the plurality of first light-emitting elements being arranged isotropically with respect to the first light-receiving element and surrounding the first light-receiving element, and the plurality of second light-emitting elements being arranged isotropically with respect to the second light-receiving element and surrounding the second light-receiving element; and
    a processor comprising:
        a tracking unit configured to sequentially drive the plurality of first light-emitting elements and the plurality of second light-emitting elements, receive signals respectively detected by the first light-receiving element and the second light-receiving element, select candidate points of a radial artery of the object based on the received signals, and determine a tracking line by further selecting at least two points, which is a subset of the candidate points, by considering a connection relationship based on the relative positions of the candidate points and connecting the at least two points; and
        an analyzing unit configured to detect a pulse wave signal at the at least two points on the tracking line, and analyze biometric information based on the detected pulse wave signal.

2. The apparatus of claim 1, wherein the first light-receiving element and the plurality of first light-emitting elements form a first sub unit, the second light-receiving element and the plurality of second light-emitting elements form a second sub unit, and a plurality of sub units comprising the first sub unit and the second sub unit are repetitively arranged in a form of a hive.

3. The apparatus of claim 1, wherein the analyzing unit is further configured to measure a time delay between the at least two points, and calculate a pulse transit time (PTT) based on the time delay.

4. The apparatus of claim 3, wherein the analyzing unit is further configured to analyze vessel elasticity, blood flow rate, arterial stiffness, and systolic blood pressure or diastolic blood pressure of a vessel, based on the PTT.

5. The apparatus of claim 1, wherein each of the plurality of first light-emitting elements and the plurality of second light-emitting elements comprises a light-emitting diode or a laser diode, and
    each of the first light-receiving element and the second light-receiving element comprises a photodiode, a photo transistor, or a charge-coupled device.

6. The apparatus of claim 1, further comprising user interface configured to output a result regarding the analyzed biometric information.

7. The apparatus of claim 1, further comprising a communicator configured to transmit a result regarding the analyzed biometric information to an external device.

8. The apparatus of claim 1, wherein the biometric signal measurer is wearable by the object.

9. The apparatus of claim 1, wherein the apparatus is wearable by the object.

10. A radial artery tracking method comprising:
    sequentially driving a plurality of first light-emitting elements and a plurality of second light-emitting elements and radiating light from the plurality of first light-emitting elements and the plurality of second light-emitting elements to an object, wherein the plurality of first light-emitting elements are arranged isotropically with respect to a first light-receiving element and surround the first light-receiving element, and the plurality of second light-emitting elements are arranged isotropically with respect to a second light-receiving element and surround the second light-receiving element;
    detecting optical signals respectively through the first light-receiving element and the second light-receiving element according to the sequentially driving of the plurality of first light-emitting elements and the plurality of second light-emitting elements;
    selecting, by a processor, at least two highest level signals among the detected optical signals as candidate points of a radial artery of the object; and
    determining, by the processor, a tracking line by further selecting at least two points, which is a subset of the candidate points, by considering a connection relationship based on relative positions of the candidate points and connecting the at least two points.

11. A method of detecting biometric information of an object, the method comprising:
    sequentially driving a plurality of first light-emitting elements and a plurality of second light-emitting elements and radiating light from the plurality of first light-emitting elements and the plurality of second light-emitting elements to the object, wherein the plurality of first light-emitting elements are arranged isotropically with respect to a first light-receiving element and surround the first light-receiving element, and the plurality of second light-emitting elements are arranged isotropically with respect to a second light-receiving element and surround the second light-receiving element;

detecting optical signals respectively through the first light-receiving element and the second light-receiving element according to the sequentially driving of the plurality of first light-emitting elements and the plurality of second light-emitting elements;

selecting at least two highest level signals among the detected optical signals as candidate points of a radial artery of the object;

further selecting at least two points, which is a subset of the candidate points, by considering a connection relationship based on the relative positions of the candidate points;

measuring a time delay between the at least two points; and analyzing biometric information, based on the measured time delay.

12. The method of claim 11, wherein the biometric information comprises vessel elasticity, blood flow rate, arterial stiffness, and systolic blood pressure or diastolic blood pressure of a vessel.

* * * * *